United States Patent
Lamanna

(10) Patent No.: US 10,662,359 B2
(45) Date of Patent: May 26, 2020

(54) HEAT TRANSFER FLUIDS AND METHODS OF USING SAME

(71) Applicant: 3M INNOVATIVE PROPERTIES COMPANY, St. Paul, MN (US)

(72) Inventor: William M. Lamanna, Stillwater, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 16/092,005

(22) PCT Filed: Mar. 19, 2018

(86) PCT No.: PCT/IB2018/051836
§ 371 (c)(1),
(2) Date: Oct. 8, 2018

(87) PCT Pub. No.: WO2018/172919
PCT Pub. Date: Sep. 27, 2018

(65) Prior Publication Data
US 2020/0002589 A1     Jan. 2, 2020

Related U.S. Application Data

(60) Provisional application No. 62/474,097, filed on Mar. 21, 2017.

(51) Int. Cl.
C09K 5/04 (2006.01)
C09K 5/10 (2006.01)
C07C 17/281 (2006.01)
C07C 21/18 (2006.01)

(52) U.S. Cl.
CPC ............. *C09K 5/10* (2013.01); *C07C 17/281* (2013.01); *C07C 21/18* (2013.01)

(58) Field of Classification Search
CPC ... C09K 3/00; C09K 5/04; C09K 5/10; C10M 2211/06; C10M 2211/063; C10M 2213/0606
See application file for complete search history.

(56) References Cited

U.S. PATENT DOCUMENTS

| | | | |
|---|---|---|---|
| 2,918,501 A | 12/1959 | Brehm | |
| 3,917,724 A | 11/1975 | Martini | |
| 5,124,058 A * | 6/1992 | Corti | C10M 107/38 508/509 |
| 5,221,494 A * | 6/1993 | Ikeda | C10M 105/54 252/68 |
| 5,254,774 A | 10/1993 | Prokop | |
| 6,019,909 A | 2/2000 | Ide | |
| RE37,119 E | 4/2001 | Sherwood | |
| 6,374,907 B1 | 4/2002 | Tousignant | |
| 2003/0097031 A1 | 5/2003 | Ono | |
| 2010/0267597 A1* | 10/2010 | Shimura | C10M 133/46 508/283 |

FOREIGN PATENT DOCUMENTS

WO    WO 2016-196240    12/2016

OTHER PUBLICATIONS

Brunskill, "Anionic Oligornerisation of Hexafluoropropene: Fission of a Carbon-Carbon Bond by Fluoride Ion", Journal of the Chemical Society D: Chemical Communications, Aug. 1970, No. 21, pp. 1444-1446.
Dmowski, "The use of crown ethers in the synthesis of hexafluoropropene and tetrafluoroethylene oligomers", Journal of Fluorine Chemistry, Jan. 1977, vol. 9, No. 1, pp. 94-96.
Makarov, "Hexafluoropropene Trimer. Synthesis and Properties of Functional Derivatives", Journal of Fluorine Chemistry, Oct. 1977, vol. 10, No. 4, pp. 323-327.
Martini, "Isomerisation of dimer and trimer of hexafluorpropens depiction and reactions of an tetrameren", Tetrahedron Letters, 1974, vol. 15, No. 24, pp. 2129-2132.
Young, "Atmospheric Lifetime and Global Warming Potential of a Perfluoropolyether", Environmental Science & Technology, 2006, vol. 40, No. 7, pp. 2242-2246.
International Search Report for PCT International Application No. PCT/IB18/51836, dated Jun. 26, 2018, 2 pages.

* cited by examiner

*Primary Examiner* — John R Hardee
(74) *Attorney, Agent, or Firm* — Adam Bramwell

(57) ABSTRACT

An apparatus for heat transfer includes a device and a mechanism for transferring heat to or from the device. The mechanism for transferring heat includes a working fluid that includes a hexafluoropropylene trimer having Structural Formula (1) The hexafluoropropylene trimer having Structural Formula (1) is present in the working fluid in an amount of at least 85% by weight, based on the total weight of hexafluoropropylene trimer in the working fluid.

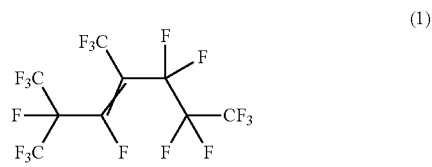

(1)

6 Claims, No Drawings

HEAT TRANSFER FLUIDS AND METHODS OF USING SAME

CROSS REFERENCE TO RELATED APPLICATIONS

This application is a national stage filing under 35 U.S.C. 371 of PCT/IB2018/051836, filed Mar. 19, 2018, which claims the benefit of U.S. Provisional Application No. 62/474,097, filed Mar. 21, 2018, the disclosure of which is incorporated by reference in its entirety herein.

FIELD

The present disclosure relates to heat transfer fluids and methods of making and using the same.

BACKGROUND

Various compositions comprising trimers of HFP and their use as inert or isolating liquids, solvents, and cooling agents are described in, for example, U.S. Pat. Nos. 3,917,724, 2,918,501, I. L. Knunyants, et. al., J. Fluorine Chemistry, 10, 323-327 (1977), R. N. Haszeldine, et. al., J. Fluorine Chemistry, 9, 94-96 (1977), and T. Martini, et. al., Tetrahedron Letters (24), 2129-2132 (1974).

SUMMARY

In some embodiments, an apparatus for heat transfer is provided. The apparatus includes a device and a mechanism for transferring heat to or from the device. The mechanism for transferring heat includes a working fluid that includes a hexafluoropropylene trimer having Structural Formula (1)

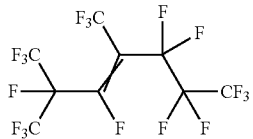

(1)

The hexafluoropropylene trimer having Structural Formula (1) is present in the working fluid in an amount of at least 85% by weight, based on the total weight of hexafluoropropylene trimer in the working fluid.

In some embodiments, a method of transferring heat is provided. The method includes providing a device and transferring heat to or from the device using a working fluid that includes the above-described hexafluoropropylene trimer compound or working fluid.

The above summary of the present disclosure is not intended to describe each embodiment of the present disclosure. The details of one or more embodiments of the disclosure are also set forth in the description below. Other features, objects, and advantages of the disclosure will be apparent from the description and from the claims.

DETAILED DESCRIPTION

In view of an increasing demand for environmentally friendly and low toxicity chemical compounds, it is recognized that there exists an ongoing need for new heat transfer fluids that provide further reductions in adverse environmental and health impact, and which can also meet the performance requirements (e.g., non-flammability, thermal and chemical stability, good dielectric properties, low pour point, low viscosity and useful operating temperature range) of a variety of different applications (e.g., heat transfer fluids, two-phase immersion cooling, chiller fluids, Rankine cycle working fluids), and be manufactured cost-effectively.

In electronic applications, the ability of a heat transfer fluid to provide low pour point, low viscosity, and good dielectric properties (e.g., low dielectric constant, high dielectric strength, and high volume resistivity) can be particularly important in order to maintain acceptable low temperature heat transfer performance without adversely impacting the electrical performance of the electronic device. In such applications, historically, perfluorocarbons (or PFCs) and perfluoropolyethers (PFPEs) have been the heat transfer fluids of choice, since they can provide excellent low temperature and dielectric properties while also providing low toxicity, excellent stability, and non-flammability at a reasonable cost. However, such materials have very high global warming potentials (GWPs) and are therefore expected to eventually be phased out, either voluntarily or through government regulations.

More environmentally sustainable heat transfer fluids exist, such as hydrofluoroethers (HFEs), perfluoroketones (PFKs), hydrofluoroether olefins (HFEOs), and hydrofluoroolefins (HFOs), but these alternatives have proven not to be universal replacements for the PFCs and PFPEs because they cannot match the excellent dielectric properties of these materials or they do not provide adequate thermal and hydrolytic stability. Thus, there is an existing need for new heat transfer fluids that can provide a balance of properties that closely match those of the PFCs and the PFPEs, while also providing a significant reduction in GWP, acceptably low toxicity, and adequate thermal stability.

Generally, the present disclosure provides an isomerically pure hexafluoropropylene (HFP) trimer as a heat transfer fluid. This material provides surprisingly good low temperature properties, including very low pour point and low viscosity at low temperatures compared to commonly available mixtures of HFP Trimer isomers and other highly fluorinated fluids. In addition, it provides good dielectric properties (low dielectric constant, high dielectric strength, high volume resistivity), low acute toxicity, and has a short environmental lifetime and thus a low global warming potential. Furthermore, the isomerically pure HFP Trimer of the present disclosure can be manufactured at low cost via a one step, 100% atom efficient process involving catalytic oligomerization of inexpensive HFP monomer. This unique balance of attributes make the compositions of the present disclosure attractive candidates for replacement of PFCs and PFPEs currently in use in various heat transfer applications where alternative low GWP fluids are needed to meet existing or imminent new regulations.

As used herein, a criss-crossed double bond in a structural formula indicates that the formula may be present as the E diastereomer, the Z diastereomer, or a mixture of the E and Z diastereomers in any proportion.

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In some embodiments, the present disclosure is directed to compositions that include a structural isomer of HFP trimer having Structural Formula (1):

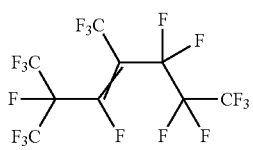

(1)

In some embodiments, the HFP trimer of Structural Formula (1) may be present in either or both of the two diastereomeric forms, the E or Z diastereomers, which are depicted below in Structural Formulas (1A) and (1B), respectively:

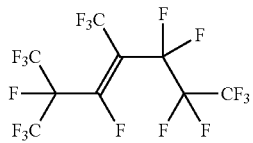

Formula 1A

E-Diastereomer

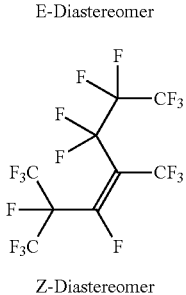

Formula 1B

Z-Diastereomer

In various embodiments, the compositions may include a mixture of the E and Z diastereomers in any proportion. Alternatively, the compositions may include only the E diastereomer or only the Z diastereomer.

In some embodiments, the compositions may not include appreciable amounts of other structural isomers of HFP trimer, including the structural isomers of Structural Formula (2) and Structural Formula (3).

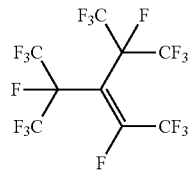

Formula 2

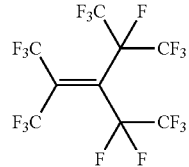

Formula 3

In this regard, in some embodiments, the compositions may include at least 85%, at least 90%, at least 95%, at least 97%, at least 98%, at least 99%, or at least 99.9 weight % of the structural isomer of Formula (1), based on the total weight of all HFP trimer structural isomers present in the composition. Surprisingly, it has been discovered that the structural isomer of Formula 1 provides superior low temperature performance when compared to more commonly available forms of HFP trimer, which typically comprise a complex mixture of structural isomers consisting mainly of structural isomers of Formula 1, 2, and 3, as well as other minor structural isomers of HFP Trimer. The improved low temperature performance of Structural Formula 1 includes a significantly lower pour point and significantly lower viscosity at low temperatures; properties which directly impact the ability of a heat transfer fluid to remain fluid and effectively transfer heat at low temperatures. In addition, the HFP trimers of Structural Formula 1 have been found to provide strong dielectric properties (low dielectric constant, high dielectric strength, and high volume resistivity), while also providing non-flammability, adequate stability, low acute toxicity, and a short environmental lifetime and thus a low global warming potential. This unique balance of properties renders the HFP trimers of Structural Formula 1 an attractive option for replacement of PFCs and PFPEs currently in use in various applications where alternative low GWP fluids are needed to meet the changing regulation landscape.

In some embodiments, the isomerically pure HFP trimer containing compositions of the present disclosure may be hydrophobic, relatively chemically unreactive, and thermally stable. The compositions may have a low environmental impact. In this regard, the isomerically pure HFP trimer containing compositions may have a global warming potential (GWP, 100 year ITH) of less than 1000 or less than 500. As used herein, GWP is a relative measure of the global warming potential of a compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i[C(t)]dt}{\int_0^{ITH} a_{CO_2}[C_{CO_2}(t)]dt} = \frac{\int_0^{ITH} a_i C_{oi} e^{-t/\tau_i} dt}{\int_0^{ITH} a_{CO_2}[C_{CO_2}(t)]dt}$$

In this equation $a_i$ is the radiative forcing per unit mass increase of a compound in the atmosphere (the change in the flux of radiation through the atmosphere due to the IR absorbance of that compound), C is the atmospheric concentration of a compound, τ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In some embodiments, the present disclosure is further directed to methods of making the above-described HFP Trimer of structural Formula (1) in high overall yield (based on HFP starting material) and with high selectivity (relative to all the structural isomers of HFP Trimer produced). In some embodiments, the method may be carried out in a single catalytic step starting from HFP monomer. In various embodiments, the method may include feeding HFP monomer to a reaction mixture that includes a catalytic amount of catalyst and a suitable organic solvent (e.g., Dimethylformamide (DMF)) at a temperature that is sufficient to oligomerize the HFP according to Equation 1:

Equation 1

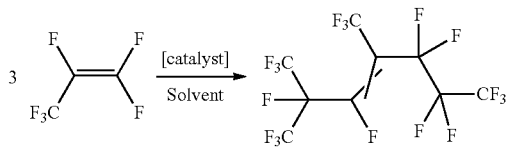

In some embodiments, following completion of the reaction, the crude fluorochemical product mixture may then undergo liquid-liquid phase separation from the catalyst/solvent phase, allowing for isolation (by, for example, simple filtration and liquid-liquid phase separation) of a composition that includes at least 70, at least 75, at least 80, at least 85, at least 90, or at least 95 weight % of HFP Trimer of structural Formula (1), based on the total weight of crude fluorochemical product isolated (which may include various HFP oligomers (e.g., dimers, trimers, tetramers) and other side products). Furthermore, the HFP trimer fraction produced may include at least 85%, at least 90%, at least 95%, at least 97%, at least 98%, at least 99%, or at least 99.9% by weight of HFP Trimer of structural Formula 1 vs. all structural isomers of HFP Trimer (MW 450 g/mol) present.

In some embodiments the catalyst may include a metal fluoride, such as an alkali metal fluoride or later metal fluorides from the periodic table. In various embodiments, the catalyst includes (or consists essentially of) cesium fluoride. In some embodiments the reaction mixture may further comprise a co-catalyst. In some embodiments, the co-catalyst may be a crown ether. In some embodiments the organic solvent is DMF. In some embodiments the reaction temperature may be at least 60, at least 70, at least 80, or at least 90° C. during the addition of HFP monomer. In some embodiments the HFP monomer may be continuously fed to the reaction mixture at a feed rate of less than 30% per hour, less than 20% per hour, less than 15% per hour, or less than 10% per hour, based on the total HFP charge employed.

By employing the methods of the present disclosure, an isomerically pure HFP trimer containing composition can be manufactured in high yield at low cost via a one step, 100% atom efficient process involving catalytic oligomerization of inexpensive hexafluoropropylene (HFP) monomer.

In some embodiments, the present disclosure is further directed to working fluids that include the above-described HFP trimer-containing compositions as a major component. For example, the working fluids may include at least 25%, at least 50%, at least 70%, at least 80%, at least 90%, at least 95%, or at least 99% by weight of the above-described HFP trimer-containing compositions, based on the total weight of the working fluid. In addition to the HFP trimer-containing compositions, the working fluids may include a total of up to 75%, up to 50%, up to 30%, up to 20%, up to 10%, or up to 5% by weight of one or more of the following components: alcohols, ethers, alkanes, alkenes, haloalkenes, perfluorocarbons, perfluorinated tertiary amines, perfluoroethers, cycloalkanes, esters, ketones, oxiranes, aromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof, based on the total weight of the working fluid. Such additional components can be chosen to modify or enhance the properties of a composition for a particular use.

In some embodiments, the present disclosure is further directed to an apparatus for heat transfer that includes a device and a mechanism for transferring heat to or from the device. The mechanism for transferring heat may include a heat transfer working fluid that includes an HFP trimer-containing composition of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, heat exchangers, and electrochemical cells. In some embodiments, the device can include a chiller, a heater, or a combination thereof.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility suggests that the heat-transfer fluid candidate exhibit low dielectric constant, high dielectric strength, high volume resistivity, and poor solvency for polar materials. Additionally, the heat-transfer fluid should exhibit good mechanical compatibility, that is, it should not affect typical materials of construction in an adverse manner.

The provided apparatus may include a mechanism for transferring heat. The mechanism may include a heat transfer fluid. The heat transfer fluid may include one or more HFP trimer-containing compositions of the present disclosure. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 230° C.

Heat can be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath.

In using the compositions and fluids of the present disclosure as heat transfer agents, in some embodiments, the processes and devices described in, for example, U.S. Reissue Patent 37,119 E (Sherwood) and U.S. Pat. No. 6,374,907 (Tousignant), each of which are hereby incorporated by reference in their entirety, may be employed.

Listing of Embodiments

1. An apparatus for heat transfer comprising:
   a device; and
   a mechanism for transferring heat to or from the device, the mechanism comprising a working fluid comprising a hexafluoropropylene trimer having Structural Formula (1)

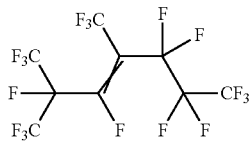

wherein the hexafluoropropylene trimer having Structural Formula (1) is present in the working fluid in an amount of at least 85% by weight, based on the total weight of hexafluoropropylene trimer in the working fluid.
2. The apparatus for heat transfer of embodiment 1, wherein the hexafluoropropylene trimer having Structural Formula (1) is present in the working fluid in an amount of at least 25% by weight, based on the total weight of the working fluid.
3. The apparatus for heat transfer according to any one of embodiment 1-2, wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.
4. The apparatus for heat transfer according to any one of embodiment 1-3, wherein the mechanism for transferring heat is a component in a system for maintaining a temperature or temperature range of a device.
5. A method of transferring heat comprising:
   providing a device; and
   transferring heat to or from the device using a working fluid that comprises a hexafluoropropylene trimer having Structural Formula (1)

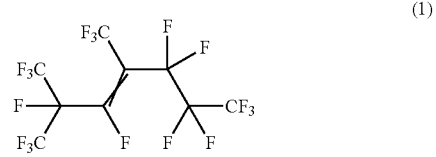 [SMILES: FC(=C(C(F)(F)F)C(F)(F)C(F)(F)C(F)(F)F)C(F)(C(F)(F)F)C(F)(F)F]

wherein the hexafluoropropylene trimer having Structural Formula (1) is present in the working fluid in an amount of at least 85% by weight, based on the total weight of hexafluoropropylene trimer in the working fluid.
6. A method of making an isomerically pure hexafluoropropylene trimer, the method comprising:
   reacting hexafluoropropylene monomer with a catalyst, in the presence of a solvent, to form a crude fluorochemical reaction product comprising hexafluoropropylene trimer having Structural Formula (1)

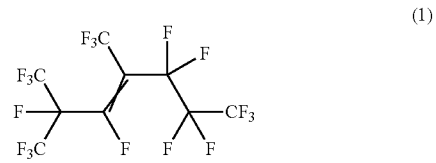 [SMILES: FC(=C(C(F)(F)F)C(F)(F)C(F)(F)C(F)(F)F)C(F)(C(F)(F)F)C(F)(F)F]

and;
   isolating the crude fluorochemical reaction product from the catalyst and solvent;
   wherein the step of reacting hexafluoropropylene monomer with a catalyst comprises continuously feeding the hexafluoropropylene monomer to a reaction mixture at a feed rate of less than 30% by weight per hour, based on the total weight of hexafluoropropylene monomer fed to the reaction mixture;
   wherein the step of reacting hexafluoropropylene monomer with a catalyst is carried out at a reaction temperature of at least 60° C.;
   wherein the hexafluoropropylene trimer having Structural Formula (1) is present in an amount of at least 70% by weight, based on the total weight of the isolated crude fluorochemical reaction product; and
   wherein the hexafluoropropylene trimer having Structural Formula (1) is present in an amount of at least at least 85% by weight, based on the total weight of the hexafluoropropylene trimer present in the isolated crude fluorochemical reaction product.

The operation of the present disclosure will be further described with regard to the following detailed examples. These examples are offered to further illustrate various embodiments and techniques. It should be understood, however, that many variations and modifications may be made while remaining within the scope of the present disclosure.

EXAMPLES

Objects and advantages of this disclosure are further illustrated by the following comparative and illustrative examples. Unless otherwise indicated, all materials were obtained from Sigma-Aldrich, USA.

Example 1: Synthesis of 1,1,1,2,3,5,5,6,6,7,7,7-dodecafluoro-2,4-bis(trifluoromethyl)hept-3-ene

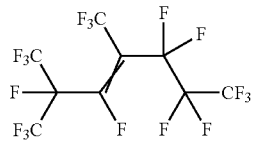

The selective one step synthesis of 1,1,1,2,3,5,5,6,6,7,7,7-dodecafluoro-2,4-bis(trifluoromethyl)hept-3-ene (HFP Trimer structural Formula 1) was performed as follows. A 600 mL Hastelloy Parr reactor was transferred to a drybox and charged with 15.774 g CsF (obtained from Advance Research Chemicals, Inc., Catoosa, Okla.) and 171.40 g anhydrous dimethylformamide (DMF) solvent. The reactor was sealed then removed from the drybox, tared, and mounted in reactor stand. The Parr reactor was chilled in a dry ice bath at −30° C., evacuated briefly to remove non-condensable gases, and then equipped with heating mantle and heated to 90° C. with maximum agitation. Once the 90° C. set point temperature was reached, the continuous addition of HFP monomer to the headspace of the Parr reactor was begun through a metering valve at an average addition rate of 1.5 g/min. A moderate exotherm was observed during the continuous addition of HFP causing the reaction temperature to rise to a maximum of 117° C. (no active cooling present). The pressure in the reactor was less than 20 psi during the course of the entire reaction, indicating that HFP was being consumed as it was added. Once a total of 498.5 g of HFP monomer had been added to the reaction mixture, HFP addition was stopped and the reaction solution was held at 90° C. for 1 hour with continued stirring to allow residual HFP in the reactor to react. Then, heating was terminated and the reaction mixture was allowed to cool gradually to room temperature overnight with stirring. Once cooled to room temperature, the reactor was dismantled and the liquid contents poured into a 750 mL Erlenmeyer flask revealing two liquid phases; a dark orange-brown upper DMF phase and a clear colorless lower fluorochemical phase along with some suspended CsF catalyst. This mixture was filtered by suction through a pad of Celite to remove suspended solids and the filtrate was transferred to a 500 mL separatory funnel and allowed to phase separate. The lower fluorochemical phase was isolated and packaged in a 500 mL HDPE polybottle for storage. The isolated yield of this crude fluorochemical product (Example 1) was 460.78 g, corresponding to 92.43% of theoretical yield based on HFP monomer. GC-FID analysis of the neat crude fluorochemical product revealed a single major peak (85.58 Area %) corresponding to 1,1,1,2,3,5,5,6,6,7,7,7-dodecafluoro-2,4-bis(trifluoromethyl)hept-3-ene (HFP Trimer Structural Formula 1). More complete composition details as determined by GC-FID analysis of the crude product and confirmed by GC-MS and $^{19}$F NMR analysis are provided in Table 1.

TABLE 1

Composition of Crude Fluorochemical Product (Example 1) via GC-FID analysis

| | Area % |
|---|---|
| HFP Dimer (MW 300) | 1.77 |
| HFP Dimer + CF$_2$ (MW 350) | 0.51 |
| HFP Dimer + 2 CF$_2$ (MW 400) | 0.42 |
| HFP Trimer Structural Formula 1 (MW 450) | 85.58 |
| HFP Trimer Structural Formula 2 (MW 450) | 0.41 |
| HFP Trimer Unidentified Isomer (MW 450) | 0.85 |
| HFP Trimer Structural Formula 3 (MW 450) | 0.78 |
| HFP Trimer + CF$_2$ (MW 500) | 0.57 |
| HFP Tetramers (MW 600) | 8.27 |

The data summarized in Table 1 indicates that HFP Trimer of structural Formula 1 comprises 85.58% of the isolated crude fluorochemical product and it is formed with a selectivity of 97.7% with respect to all the structural isomers of HFP Trimer (molecular weight 450 g/mol) produced in this reaction.

Examples 2 and 3

In order to purify the HFP Trimer produced in this reaction and remove the lower and higher MW components of the crude product mixture, the crude product was fractionally distilled at atmospheric pressure under nitrogen using a 20-tray Oldershaw column and a distillation head equipped with a condenser chilled to 0° C. and an automated liquid splitter operating at a 60:1 split ratio. Two heart cut distillate fractions were collected, heart cut #1 (85.57 g) collected at a head temperature of 105.3-106.2° C. and heart cut #2 (252.74 g) collected at a head temperature of 106.2-106.4° C. Both heart cut fractions were analyzed by GC-FID and were found to contain 1,1,1,2,3,5,5,6,6,7,7,7-dodecafluoro-2,4-bis(trifluoromethyl)hept-3-ene (HFP Trimer structural Formula 1) in very high overall purity as summarized in Table 2.

TABLE 2

Composition of Distilled Fluorochemical Product (GC-FID Area %)

| Example # | Distillation Heart Cut # | Head Temperature Range, ° C. | Weight Collected, g | % HFP Trimer Structural Formula 1 |
|---|---|---|---|---|
| Example 2 | 1 | 105.3-106.2 | 85.57 | 97.92 |
| Example 3 | 2 | 106.2-106.4 | 252.74 | 98.45 |

Heart Cut #2 (Example 3) was further analyzed by quantitative $^{19}$F NMR spectroscopy and was shown to comprise 98.4 wt % 1,1,1,2,3,5,5,6,6,7,7,7-dodecafluoro-2,4-bis(trifluoromethyl)hept-3-ene (HFP Trimer structural Formula 1) as a mixture of the E (77.6 wt %) and the Z (20.8 wt %) diastereomers.

Comparative Examples

Descriptions of Comparative Examples CE1-CE4 are provided in Table 3. These Comparative Examples included HFP trimer comprising a mixture of 3 major isomers (CE1) and three commercial heat transfer fluids (CE2, CE3, and CE4).

TABLE 3

Comparative Examples

| Comparative Example | Description | Source |
|---|---|---|
| CE1 | 15.0 wt % structural Formula 1, 24.9 wt % structural Formula 2, and 59.1 wt % structural Formula 3* | prepared by a method similar to that described for Example 1, but using KF as the catalyst |
| CE2 | FC-3283: FLUORINERT Perfluorocarbon (PFC) Electronic Liquid | 3M Company, St. Paul, MN, USA |
| CE3 | HFX-110: OPTEON Sinera Hydrofluoroether Olefin (HFEO) Heat Transfer Fluid | du Pont/Chemours Company, Wilmington, DE, USA |
| CE4 | GALDEN HT-110 perfluoropolyether (PFPE) | Solvay, Brussels, Belgium |

*measured by quantitative $^{19}$F NMR analysis

Test Procedures

Atmospheric lifetimes of Example 3 and CE2 were determined from the rate of reaction of test samples with hydroxyl radicals. The pseudo-first order rates for the reaction of the gaseous test samples with hydroxyl radical were measured in a series of experiments relative to reference compounds such as chloromethane and ethane. The measurements were performed in a 5.7 L, heated FTIR gas cell equipped with a polished semiconductor-grade quartz window. An Oriel Instruments UV Lamp, Model 66921 equipped with a 480 W mercury-xenon bulb was used to generate hydroxyl radicals by photolyzing ozone in the presence of water vapor. The concentrations of the test sample and the reference compound were measured as a function of reaction time using an I-Series FTIR from Midac Corporation. The atmospheric lifetimes were calculated from the reaction rates for the test samples relative to the reference compounds and the reported lifetime of the reference compounds as shown below:

$$\tau_x = \tau_r \cdot \frac{k_r}{k_x}$$

where $\tau_x$ is the atmospheric lifetime of the test sample, $\tau_r$ is the atmospheric lifetime of the reference compound, and $k_x$ and $k_r$ are the rate constants for the reaction of hydroxyl radical with the test sample and the reference compound, respectively.

Global warming potentials (GWPs) have been estimated for Example 3 and CE2 using these atmospheric lifetimes. The GWPs were calculated according to the Intergovernmental Panel on Climate Change (IPCC) 2013 method using a 100 year integration time horizon (ITH). The radiative efficiencies used in these calculations were based upon the infrared cross-sections measured on the test samples. The GWP of CE3 was obtained from du Pont de Nemours trade literature. A published GWP for CE4 could not be found, so the GWP of CE4 was based on the published GWP of a lower molecular weight perfluoropolyether of similar structure ($CF_3OCF(CF_3)CF_2OCF_2OCF_3$; C. J. Young, et. al., Environ. Sci. Technol. 2006, 40, 2242-2246).

The 4 hour acute inhalation toxicity of Example 3 and CE2 in rats was determined by dosing animals at 10,000 or 619 ppm vol/vol in air (per Table 4) for 4 hours followed by 14 day post-dose monitoring. Based on the animal test results and the vapor concentration of the test compound, the LC-50 values were estimated. The NOEL (No Effect Level) value of CE3 was obtained from du Pont de Nemours trade literature. The 4 hr inhalation LC-50 value for CE4 was obtained from Solvay MSDS.

Kinematic viscosity of Example 3, CE1, and CE2 was measured using a Schott AVS 350 Viscosity Timer, Analytical Instrument No. 341. For temperatures below 0° C., a Lawler temperature control bath Analytical Instrument No. 320 was used. The viscometers used for all temperatures are 545-03, 10 and 13. Viscometers were also corrected using the Hagenbach correction. Kinematic viscosity data for CE3 and CE4 was obtained from du Pont and Solvay trade literature, respectively.

Boiling points of Example 3, CE1, and CE2 were measured using ASTM D1120-94 "Standard Test Method for Boiling Point of Engine Coolants. Boiling points of CE3 and CE4 were obtained from du Pont and Solvay trade literature, respectively.

Pour/Freeze Point was defined as the lowest temperature where the sample was visually observed to flow in 5 seconds after being turned horizontally in sealed tube. Example 3, CE1, and CE2 were cooled below the pour point and warmed at a rate of approximately 2 deg C./min in a manually temperature controlled bath. Samples were visually inspected approximately every 1-2 minutes. Temperature was recorded using an RTD thermometer, Analytical Instrument No. 898. Pour/Freeze points of CE3 and CE4 were obtained from du Pont and Solvay trade literature, respectively.

The dielectric properties and electrical conductivity measurements were performed with an Alpha-A High Temperature Broadband Dielectric Spectrometer modular measurement system from Novocontrol. The sample cell BDS 1200 utilizing gold plated parallel plates of 40 mm diameter was interfaced to the Alpha-A mainframe while utilizing the ZG2 Dielectric/Impedance General Purpose Interface. Each 3M test sample was prepared between parallel plate electrodes as described above and the complex permittivity (dielectric constant and loss) were evaluated from the phase sensitive measurement of the electrodes voltage difference (Vs) and current (Is). Frequency domain measurements were carried out at discrete frequencies from 0.00001 Hz to 20 MHz. Impedances from 10 milliOhms up to 1×10 E14 ohms can be measured up to a maximum of 4.2 volts AC. For this experiment, however, a fixed AC voltage of 1.0 volts was used. The DC conductivity was extracted from an optimized broadband dielectric relaxation fit function that contains at least 1 term of the low frequency Havrrilak Negami dielectric relaxation function and one separate frequency dependent conductivity term. The volume resistivity was calculated from the DC conductivity. The dielectric constants and volume resistivities of CE3 and CE4 were obtained from du Pont and Solvay trade literature, respectively.

The dielectric breakdown strength (dielectric strength) measurements of Example 3, CE1, and CE2 were performed according to ASTM D149 with the Phenix Technologies Model LD-60 that was specifically designed for testing in the 7-69 kV, 60 Hz breakdown range. The dielectric strengths of CE3 and CE4 were obtained from du Pont and Solvay trade literature, respectively.

Results

TABLE 4

Comparative Properties of Select Fluorinated Fluids

| Properties | Units | Example 3: ≥98% HFP Trimer Structural Formula 1 | CE1: HFP Trimer Mixed Isomers | CE2: FC-3283 | CE3: HFX-110 | CE4: GALDEN HT-110 |
|---|---|---|---|---|---|---|
| Boiling Point | °C. | 108 | 112 | 128 | 110 | 110 |
| Pour/Freeze Point | °C. | −109 | −100 | −50 | <−90 | −100 |
| Dielectric Constant | at 1 KHz | 2.04 | 1.97 | 1.9 | 5.48 | 1.92 |
| Dielectric Strength at 25° C. | kV, 0.1" gap | 40 | 40 | 43 | 29 | 40 |
| Viscosity @ 25° C. | cSt | 0.6 | 1.0 | 0.8 | 0.7 | 0.8 |
| Viscosity @ −10° C. | cSt | 1.4 | 3.4 | | | |
| Viscosity @ −20° C. | cSt | 1.9 | 4.9 | | | 1.9 |
| Viscosity @ −40° C. | cSt | 4.8 | 11.3 | 5.3 | ~3.4 | 3.7 |
| Volume Resistivity | ohm-cm | 10^14 | 10^14 | 10^15 | 10^10 | 10^15 |
| GWP | 100 yr | 420 | | >8000 | 2.5* | >8000 |
| LC-50 (4 hr Inhalation in Rats) | ppmv | >10,000 | | >619 | 5000* (NOEL) | >2445 |

*Value obtained from Nemours product literature. All LC-50s have been interpreted to represent the highest exposure levels tested.

It is clear from the results summarized in Table 4 that Example 3 provides excellent low temperature properties. Its pour point is lower than any of the other materials listed and is surprisingly lower than CE1, the sample of HFP Trimer mixed isomers. This advantage is also reflected in the viscosity data, showing that the single isomer of HFP Trimer (Example 3) has significantly lower viscosity than the mixed isomers (CE1), especially at lower temperatures and is roughly on par with the commercial products (CE2-CE4). Another advantage of Example 3 is its excellent dielectric properties as reflected by the values for dielectric constant, dielectric strength and volume resistivity. As one can see, these are very similar to the values for the commercial perfluorocarbon (PFC) and perfluoropolyether (PFPE) products, CE2 and CE4, respectively, but far better than the values listed for the hydrofluoroether olefin (HFEO) product, CE3. Yet another significant advantage of the Example 3 is its much lower GWP compared to Comparative Examples CE2-CE4. This corresponds to more than an order of magnitude reduction in environmental impact. Thus the HFP Trimer of structural Formula 1 is able to deliver physical properties similar to or better than the perfluorinated PFC and PFPE products while also providing significantly improved environmental sustainability and low toxicity.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows. All references cited in this disclosure are herein incorporated by reference in their entirety.

What is claimed is:
1. An apparatus for heat transfer comprising:
a device; and
a mechanism for transferring heat to or from the device, the mechanism comprising a working fluid comprising a hexafluoropropylene trimer having Structural Formula (1)

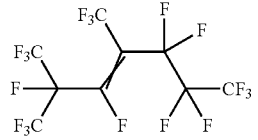 [SMILES: FC(=C(C(F)(F)F)C(F)(F)C(F)(F)C(F)(F)F)C(F)(C(F)(F)F)C(F)(F)F]

wherein the hexafluoropropylene trimer having Structural Formula (1) is present in the working fluid in an amount of at least 85% by weight, based on the total weight of hexafluoropropylene trimer in the working fluid.

2. The apparatus for heat transfer of claim 1, wherein the hexafluoropropylene trimer having Structural Formula (1) is present in the working fluid in an amount of at least 25% by weight, based on the total weight of the working fluid.

3. The apparatus for heat transfer according to claim 1, wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

4. The apparatus for heat transfer according to claim 1, wherein the mechanism for transferring heat is a component in a system for maintaining a temperature or temperature range of a device.

5. A method of transferring heat comprising:

providing a device; and transferring heat to or from the device using a working fluid that comprises a hexafluoropropylene trimer having Structural Formula (1)

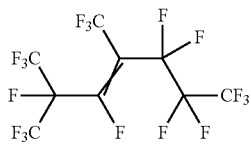
(1)

wherein the hexafluoropropylene trimer having Structural Formula (1) is present in the working fluid in an amount of at least 85% by weight, based on the total weight of hexafluoropropylene trimer in the working fluid.

6. A method of making an isomerically pure hexafluoropropylene trimer, the method comprising:

reacting hexafluoropropylene monomer with a catalyst, in the presence of a solvent, to form a crude fluorochemical reaction product comprising hexafluoropropylene trimer having Structural Formula (1)

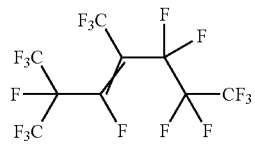
(1)

and;

isolating the crude fluorochemical reaction product from the catalyst and solvent;

wherein the step of reacting hexafluoropropylene monomer with a catalyst comprises continuously feeding the hexafluoropropylene monomer to a reaction mixture at a feed rate of less than 30% by weight per hour, based on the total weight of hexafluoropropylene monomer fed to the reaction mixture;

wherein the step of reacting hexafluoropropylene monomer with a catalyst is carried out at a reaction temperature of at least 60° C.;

wherein the hexafluoropropylene trimer having Structural Formula (1) is present in an amount of at least 70% by weight, based on the total weight of the isolated crude fluorochemical reaction product; and wherein the hexafluoropropylene trimer having Structural Formula (1) is present in an amount of at least at least 85% by weight, based on the total weight of the hexafluoropropylene trimer present in the isolated crude fluorochemical reaction product.

* * * * *

UNITED STATES PATENT AND TRADEMARK OFFICE
CERTIFICATE OF CORRECTION

PATENT NO. : 10,662,359 B2
APPLICATION NO. : 16/092005
DATED : May 26, 2020
INVENTOR(S) : William Mario Lamanna It is certified that error appears in the above-identified patent and that said Letters Patent is hereby corrected as shown below:

On the Title Page

Column 2 (item (56) Other Publications)
Line 1, Delete "Oligornerisation" and insert -- Oligomerisation --, therefor.

Column 2 (Abstract)
Line 5, After "(1)" insert -- . --.

In the Specification

Column 1
Line 11, Delete "2018," and insert -- 2017, --, therefor.

Column 8
Line 5, Delete "embodiment" and insert -- embodiments --, therefor.
Line 13, Delete "embodiment" and insert -- embodiments --, therefor.
Line 67, Delete "at least at least" and insert -- at least --, therefor.

In the Claims

Column 16
Line 26, In Claim 6, delete "at least at least" and insert -- at least --, therefor.

Signed and Sealed this
Twenty-fifth Day of October, 2022

Katherine Kelly Vidal
*Director of the United States Patent and Trademark Office*